United States Patent [19]
Kourbatov et al.

[11] Patent Number: 5,744,672
[45] Date of Patent: *Apr. 28, 1998

[54] METHOD FOR INHIBITING THE POLYMERIZATION OF VINYL AROMATICS

[76] Inventors: Vladimir Anatolievich Kourbatov, Dorogomiloyskaya D. 5., Kv. 49, 112059 Moscow, Russian Federation; Nataljya Pavlovna Boreyko, Sohkolnii 6-34, 423550 Nischnekamsk, Russian Federation; Valerii Pavlovich Zouev, Chimikov 64, ap. 94, 423550 Nischnekamsk, Russian Federation; Alexandr Grigorievich Liakumovich, Galee Str. 10, ap. 8, 420072 Kazan, Russian Federation

[*] Notice: The term of this patent shall not extend beyond the expiration date of Pat. No. 5,488,192.

[21] Appl. No.: 586,781
[22] PCT Filed: Jul. 18, 1994
[86] PCT No.: PCT/IB94/00240
§ 371 Date: Jan. 23, 1996
§ 102(e) Date: Jan. 23, 1996
[87] PCT Pub. No.: WO95/03263
PCT Pub. Date: Feb. 2, 1995

[30] Foreign Application Priority Data

Jul. 23, 1993 [RU] Russian Federation ..... RU-930-37814

[51] Int. Cl.$^6$ .............. C07C 5/333; C07C 7/20
[52] U.S. Cl. ............... 585/440; 585/435; 585/2; 585/3; 585/4; 585/5; 585/832; 203/9; 208/48 AA
[58] Field of Search ............... 585/5, 435, 2, 585/3, 4, 440, 832, 950; 203/9; 208/48 AA

[56] References Cited

U.S. PATENT DOCUMENTS 5,488,192   1/1996   Kourbatov et al. ............ 585/435

FOREIGN PATENT DOCUMENTS 0 550 754   7/1993   European Pat. Off. .

OTHER PUBLICATIONS

*Derwent's abstract,* No. 87-340816/48, week 8748, Abstract of SU, 1305-153 (Batalin O E), 23 Apr. 1987.
*Derwent's abstract,* No. 5276 E/03, week 8203, Abstract Of Su, 819-078 (Vernov P A), 7 Apr. 1981.
STN International, File CA, Chemical Abstracts, vol. 102, No. 20, 20 May 1985 (Columbus, Ohio, US), Volkov, R.N. et al: "Inhibiting polymerization of vinylaromatic monomers," abstract No. 167348, & Otkrytiya, Izobret. 1984, (48), 210.
STN International, file CA, Chemical Abstracts, vol. 100, No. 22, 28 May 1984 (Columbus, Ohio, US), Kurbatov, V.A. et al: "Inhibition of oxidative polymerization of styrene by phenols. Self-fluctuating conditions," abstract No. 175381, & Vysokomol. Soedin., Ser. A (1984), 26(3), 541–6.

*Primary Examiner*—Bekir L. Yildirim
*Attorney, Agent, or Firm*—Beveridge, DeGrandi, Weilacher & Young, L.L.P.

[57] ABSTRACT

A method for inhibiting the polymerization of vinyl aromatics such as styrene with a mixture of 3,5-di-tert-butyl-4-hydroxy-N,N-dimethylbenzyl amine and carboxylic acids or anhydrides thereof, in the presence of air or oxygen. The weight ratio of said 3,5-Di-tert-butylhydroxy-N,N-dimethylbenzyl amine, carboxylic acid (or carboxylic acid anhydride) and the air is 1:1 to 0.05:0.05 to 15, respectively.

10 Claims, No Drawings

METHOD FOR INHIBITING THE POLYMERIZATION OF VINYL AROMATICS

BACKGROUND OF THE INVENTION

This application is a 371 of PCT/IB 94/00240, filed on Jul. 18, 1994. The invention relates to the chemical industry, more specifically to the prevention of spontaneous polymerization of vinyl aromatic compounds during a production process. Typical of such vinyl aromatic compounds are styrene, alpha-methylstyrene, vinyltoluene and divinylbenzene. Methyl vinylpyridine is also contemplated as broadly encompassed by the vinyl aromatic terminology. Styrene will be referred to as illustrative but the foregoing compounds are understood to be included.

In the process of isolating styrene from the products of dehydrogenation of ethylbenzene, at the stage of rectification, there occurs the spontaneous polymerization of styrene monomer at high temperature. This polymerized styrene coats and/or chokes equipment, which in turn reduces heat transfer efficiency of the facilities and sometimes causes a halt of production for unscheduled cleanout. In order to avoid undesirable styrene polymerization, use is made of inhibitors.

Known in the art are methods for inhibiting the polymerization of styrene at elevated temperatures using a mixture of p-quinone dioxime with hydroquinone (USSR Inventors's Certificate 257496, 1968) or p-nitrophenol (USSR Inventor's Certificate 441263, 1972). However, they display low solubility in aromatic hydrocarbons, which result in clogging of transmission pipe lines, the trays and boilers of columns. The use of p-quinone dioxime suspensions calls for special, power consuming equipment and, most importantly, said p-quinone dioxime is inflammable and its dust-air mixtures are dangerously explosive.

A close piece of prior art discloses a method of inhibiting the polymerization of styrene with a mixture of 3,5-di-tert-butyl-4-hydroxy-N,N-dimethylbenzyl amine and aliphatic carboxylic acids (USSR Inventor's Certificate 819078, 1978).

The mixture of 3,5-di-tert-butyl-4-hydroxy-N,N-dimethylbenzyl amine with carboxylic acids in USSR Inventor's Certificate 819078, 1978 is substantially an effective polymerization inhibitor for styrene at temperatures of about 120° C. with the components thereof exhibiting: good solubility in aromatic hydrocarbons; being nontoxic; fireproof; explosionproof and inert toward the monomer. However, the doses of said inhibitor are big enough (0.5 to 0.22% by weight) that it has been established that a considerable portion of the inhibitor per se is not spent over the residence staying time in the column. This results in residual inhibitor being present in the effluent or waste from the process, and thus, there is a need to improve on said prior art inhibitor.

It is an object of the invention to improve efficiency and reduce the amount of the inhibitor consumed.

BRIEF DESCRIPTION OF THE INVENTION

This invention discloses a process for inhibiting the polymerization of a vinyl aromatic compound comprising adding to the vinyl aromatic compound an effective amount of an inhibitor system comprising: a) 3,5-di-tert-butyl-4-hydroxy-N,N-dimethylbenzyl amine; b) an acid component selected from the group consisting of carboxylic acids, synthetic fatty acids, anhydrides of an organic acid, and inorganic acids; and c) air, wherein a), b) and c) are present in the weight ratio of 1:1 to 0.05:0.05 to 15. A preferred method for inhibiting the polymerization of styrene is with a mixture of 3,5-Di-tert-buty-4-hydroxy-N,N-dimethylbenzyl amine and carboxylic acids or anhydrides thereof, in the presence of air or oxygen. The weight ratio of said 3,5-Di-tert-butyl-hydroxy-N,N-dimethylbenzyl amine, carboxylic acid (carboxylic acid anhydride) and the air (oxygen) is 1:1–0.05:0.05–15, respectively.

DETAILED DESCRIPTION OF THE INVENTION

The technological advancement in the art of styrene production is achieved by using the claimed method for inhibiting the polymerization of styrene by adding the inhibitor solution of a mixture of 3,5-di-tert-butyl-4hydroxy-,N-dimethylbenzyl amine and carboxylic acid or an anhydride of said carboxylic acid simultaneously with a supply of air in the weight ratio of 1:1 to 0.5:0.05 to 15 wherein the ratios are amine:acid component:air. A more preferred range is 1:1 to 0.2:0.05 to 15.

Said acid component may be: 1) a carboxylic acid, represented by, but not limited to, adipic acid, maleic acid, palmic acid, stearic acid, acetic acid, and phthalic acid; 2) a synthetic fatty acid; 3) the anhydride of an organic acid, such as, maleic, acetic, phthalic anhydrides; and 4) inorganic acids.

The ratio of components of the inhibiting composition of 3,5-di-tert-butyl-4-hydroxy-N,N-dimethylbenzyl amine:acid component is 1:1 to 0.05, for example. The ratio 1:1 to 0.2 is the most favorable one and provides a sufficient activity of the inhibitor in a wide range of its concentration relative to the styrene stream components.

Any organic solvent may be used to carry the two components of the inhibitor composition. Typical solvents are represented by, for instance, benzene, toluene, xylene, ethylbenzene, styrene, acetophenone, methylphenyl carbinol.

Selection of temperature conditions at the stage of preparing an inhibitor composition depends on its concentration, more concentrated solutions require elevated temperatures. For instance, a 10% solution of the inhibitor in ethylbenzene can be prepared at 20° C. and in the case of 25–30% it is necessary to heat up to 50° to 60° C.

Air is supplied into a column [fractionating column for separating benzene/toluene fraction and/or a column for separating ethylbenzene from styrene] at a level of about 0.05 to about 15 weight per unit of 3,5-di-tert-butyl-4-hydroxy-N,-N-dimethylbenzyl amine. When air is utilized, the amount of the inhibitor consumed is drastically reduced as is polymer content in the stills of the columns. In the context of this invention, it is to be understood that any use of the term "air" in conjunction with the inhibitor composition is meant to include the use of pure oxygen with the recognition that the "air" weight ratio range as expressed herein (ie 0.05 to 15) must be reduced by a factor of 5 (ie. 0.01 to 3) to account for the fact that air contains only 20% oxygen with the remainder being nitrogen or other inert gases. Oxygen is believed to be the critical component to activation of the unexpectedly improved inhibitory mechanism of this invention. While air is utilized for ease of experimentation, pure oxygen injection in a distillation column is a preferred mode of carrying out the invention.

The minimum air flow rate is 0.05 wt. parts per part of 3,5-di-tert-butyl-4-hydroxy-N,N-dimethylbenzyl amine.

The maximum flow rate of 15 weight parts of the air per part of 3,5-di-tert-butyl-4-hydroxy-N,N-dimethylbenzyl amine is limited only by any requirement imposed on the quality of the styrene monomer, an excessive amount of oxygen is bound to increase the content of carbonyl and peroxide compounds in styrene. In addition, under conditions of vacuum rectification, the feed of a gaseous substance tends to increase the residual pressure and, consequently, temperature.

The foregoing binary inhibitor plus air inhibitor system is introduced into a styrene-containing process stream or process equipment in an effective amount. As employed herein, the term "effective amount" refers to that amount of stabilizer (amine:carboxylic acid/anhydride:air) which is needed to prevent the formation of more than about 1 weight percent of vinyl aromatic polymer in less than about 3 hours at temperatures of between about 90° and about 150° C. Although the amount of stabilizer required will vary somewhat (based upon such factors as the particular vinyl aromatic compound stabilized; the particular inhibitor blend species employed; and the like) such an effective amount may be readily determined by routine experimentation. In general, such an effective amount will be between about 100 and about 2000 parts per million (ppm) by weight of vinyl aromatic compound, more preferred is 200 to 1000, most preferred is 250 to 850 and optimal is 300–500 ppm.

These weight ratios are being expressed as the amount of 3,5-di-tert-butyl-4-hydroxy-N,N-dimethylbenzyl amine to styrene. The other two components of the inhibitor system, carboxylic acid/anhydride and air are determined in accordance with the foregoing ternary ratio ranges (ie, 1:1 to 0.5:0.05 to 15), where the parts per million of the foregoing paragraph refer the level of the first numeral ("1") in the ternary ratio.

The method of testing the efficiency of inhibition is based on the determination of the quantity of a polymer forming in styrene, on initial heating, in the presence of the inhibitor.

EXAMPLES

Comparative Example 1

A three-necked flask having a dephlegmator, a thermometer and a capillary of the type used for supplying nitrogen was filled with 750 ml of styrene with the basic substance contained in the amount of 99.8% by weight (assay) and 2.04 g of a solution containing 0.204 g of 3,5-di-tert-butyl-4-hydroxy-N,N-dimethylbenzyl amine and 0.102 g of stearic acid in ethyl benzene. The contents of said flask were heated in nitrogen stream at the temperature of 101°∓2° C. and the residual pressure of 200 mm Hg for 3 hours. The pressure was then increased in the flask to atmospheric and a sample was taken for analysis for polymer content in the styrene using a gravimetric method. Polymer content in this example was found to be: 1.55% by weight.

Example 2

A three-necked flask provided with a dephlegmator a thermometer and a capillary for supplying air was filled with 750 ml of styrene with a basic substance contained in the amount of 99.8% by weight (assay) and 2.04 g of a solution containing 0.204 g of 3,5-di-tert-butyl-4-hydroxy-N,N-dimethylbenzyl amine and 0.102 g of stearic acid in ethylbenzene. The contained matter was heated in air stream to be fed at a rate of substantially about 40 ml/hr. at 101°∓2° C. and the residual pressure of 200 mm Hg for 3 hours, the weight ratio of the components of the inhibitor (3,5-di-tert-butyl-4-hydroxy-N,N-dimethylbenzyl amine and stearic acid) and air being 1:0.5:0.75. The pressure in the flask was sequentially increased to atmospheric. A sample was taken for analysis to determine polymer content in the styrene by the gravimetric method. Polymer content: 0.11% by weight.

Example 3

In the conditions of Example 2, use was made of acetic acid and air was supplied at a rate of substantially about 260 ml/hr. and more importantly, the ratio of the components of the inhibitor (3,5-di-tert-butyl-4-hydroxy-N,N-dimethylbenzyl amine and stearic acid) and air was 1:0.5:4.9. After 3 hours of initial heating, polymer content was 0.058% by weight.

Example 4

A three-necked flask equipped with a dephlegmator, a thermometer and a capillary for air supply was filled with 750 ml of styrene with a basic substance contained in the amount of 99.8% by weight and 2.04 g of a solution containing 0.204 g of 3,5-di-tert-butyl-4-hydroxy-N,N-dimethylbenzyl amine and 0.204 g of palmitic acid in ethylbenzene. The contents of the flask were heated in air stream supplied at a rate of substantially about 420 ml/hr. at 101°∓2° C. and the residual pressure of 200 mm Hg for 3 hours. The weight ratio of the components of the inhibitor (3,5-di-tert-butyl-4-hydroxy-N,N-dimethylbenzyl amine and carboxylic acid) and air was 1:1:8. The pressure in the flask was then increased to atmospheric and a sample was taken for analysis of polymer content in the styrene using a nephelometric method. No polymer was present.

Example 5

A three-necked flask having a dephlegmator, a thermometer and a capillary for air supply was filled with 750 ml of styrene with a basic substance contained in the amount of 99.7% by weight (assay) and 2.04 g of a solution containing 0.204 g of 3,5-di-tert-butyl-4-hydroxy-N,N-dimethylbenzyl amine and 0.204 g of acetic anhydride in styrene. The contents of the flask were heated in air stream supplied at the rate of 800 ml/hr, at 101°∓2° C. and the residual pressure of 200 mm Hg for 3 hours. The weight ratio of the components of the inhibitor (3,5-di-tert-butyl-4-hydroxy-N,N-dimethylbenzyl amine and acetic anhydride) and air was 1:1:15. The pressure in the flask was then increased to atmospheric and a sample was taken up for analysis of polymer content in the styrene using a nephelometric method. No polymer was present.

Example 6

According to the run of Example 2, air was supplied at the rate of 1.55 l/hr and the weight ratio of the components of the inhibitor (3,5-di-tert-butyl-4-hydroxy-N,N-dimethylbenzyl amine and stearic acid) and air being 1:0.5:30. The pressure in the flask was then increased to atmospheric and a sample was taken for analysis of polymer content in styrene according to the nephelometric method. After 3 hours of initial heating, no polymer in the styrene was found.

Example 7

In accordance with the procedure of Example 2, air was fed at the rate of 2.6 ml/hr, and at that the weight ratio of the components of the inhibitor (3,5-di-tert-butyl-4-hydroxy-N, N-dimethylbenzyl amine and stearic acid) and air was 1:0.5:0.05. The pressure in the flask was then increased to atmospheric and a sample was taken for analysis of polymer content in styrene by the gravimetric method. After 3 hours of initial heating, the styrene contains 1.45% by weight of polymer.

Comparative Example 8

A three-necked flask having a dephlegmator, a thermometer and a capillary for air supply was filled with 3,750 ml of styrene with a basic substance contained in the amount of 99.8% (assay) by weight and 3.4 g of xylene solution of an inhibitor containing 0.34 g of 3,5-di-tert-butyl-4-hydroxy-N,N-dimethylbenzyl amine and 0.374 g of stearic acid. Air was supplied at a rate of substantially about 4 ml/hr and, the weight ratio of the components of the inhibitor (3,5-di-tert-butyl-4-hydroxy-N,N-dimethylbenzyl amine and stearic acid) and air was 1:1.1:0.044. The contents of the flask were heated at the temperature 101°∓2° C. and the residual pressure of 200 mm Hg for 3 hours. The pressure in the flask was then increased to atmospheric and a sample was taken for analysis for polymer content in the styrene by the gravimetric method. After 3 hours of initial heating, the polymer content was 2.63% by weight.

Example 9

A three-necked flask equipped with a dephlegmator, a thermometer and a capillary for air supply was filled with 750 ml of styrene with a basic substance contained in the amount of 99.8% by weight (assay) and 0.34 g of 3,5-di-tert-butyl-4-hydroxy-N-N-dimethylbenzyl amine and 0.017 g of synthetic fatty acids. Oxygen was supplied at a rate of substantially about 26 ml/hr. The weight ratio of the components of the inhibitor (3,5-di-tert-butyl-4-hydroxy-N,N-dimethylbenzyl amine and synthetic fatty acid) and air was 1:0.05:0.3. The contents of the flask were heated at 101°∓2° C. and the residual pressure of 200 mm Hg for 3 hours, whereupon the pressure in the flask was increased to atmospheric and a sample was taken for analysis for polymer content in the styrene by the nephelometric method. After 3 hours of initial heating, the polymer content was 0.01% by weight.

Surprisingly this data proved that the supply of air (oxygen) considerably improves the efficiency of an inhibiting composition of 3,5-di-tert-butyl-4-hydroxy-N,N-dimethylbenzyl amine-carboxylic acid (or carboxylic acid anhydride).

We claim:

1. A process for inhibiting the polymerization of a vinyl aromatic compound comprising adding to the vinyl aromatic compound an effective amount of an inhibitor system comprising:

a) 3,5-di-tert-butyl-4-hydroxy-N,N-dimethylbenzyl amine;

b) an acid component selected from the group consisting of carboxylic acids, synthetic fatty acids, anhydrides of an organic acid, and inorganic acids; and c) air, wherein a), b) and c) are present in the weight ratio of 1:1 to 0.05:0.05 to 15.

2. A process in accordance with claim 1 wherein said vinyl aromatic compound is selected from the group consisting of styrene, alpha-methylstyrene, vinyltoluene and divinylbenzene.

3. A process in accordance with claim 1 wherein said vinyl aromatic compound is styrene.

4. A process in accordance with claim 1 wherein said 3,5-di-tert-butyl-4-hydroxy-N,N-dimethylbenzyl amine is present at a level of from 100 to 2000 parts by weight per million parts by weight of styrene.

5. A process in accordance with claim 3 wherein a) and b) are premixed to form a reaction product prior to contacting with said styrene and air.

6. A process in accordance with claim 3 wherein the weight ratio of said 3,5-di-tert-butyl-4-hydroxy-N,N-dimethylbenzyl amine to acid component is 1:1 to 0.2.

7. A process in accordance with claim 3 wherein said acid component is a carboxylic acid.

8. A process in accordance with claim 3 wherein said acid component is a synthetic fatty acid.

9. A process in accordance with claim 3 wherein said 3,5-di-tert-butyl-4-hydroxy-N,N-dimethylbenzyl amine and said acid component are present at a ratio of 1:1 to 0.5.

10. A process in accordance with claim 3 wherein said 3,5-di-tert-butyl-4-hydroxy-N,N-dimethylbenzyl amine is present at a level of from 250 to 850 parts by weight per million parts by weight of styrene.

* * * * *